United States Patent [19]

Wandell

[11] Plant 4,989

[45] Mar. 8, 1983

[54] SUGAR HACKBERRY TREE NAMED ALL SEASONS

[76] Inventor: Willet N. Wandell, Myra Station Rd., Rte. 3, Box 158, Urbana, Ill. 61801

[21] Appl. No.: 245,155

[22] Filed: Mar. 18, 1981

[51] Int. Cl.[3] ..... A01H 5/00

[52] U.S. Cl. ..... Plt./51

[58] Field of Search ..... Plt./51

*Primary Examiner*—James R. Feyrer

*Attorney, Agent, or Firm*—Wm. A. Snow

[57] ABSTRACT

A new and distinct variety of a new cultivar of sugar hackberry tree characterized by a well balanced, spreading crown having more branches than other sugar hackberry trees in the stand, a fast growth habit, freedom from Witches Broom disease found in native hackberry trees in the same growing area, and its being very hardy even in temperatures below −20° F.

4 Drawing Figures

BACKGROUND OF THE INVENTION

This new variety of hackberry tree was discovered by me growing in a nursery row of plantings of sugar hackberry seedlings at Urbana, Ill., on cultivated property. During the past several years, I have grafted cuttings from this tree at Wandell Nursery, Inc. at Urbana, Ill., in sugar hackberry trees. At the present time, I have about 500 grafts growing true to form and they are rapid growers even as a juvenile.

BRIEF DESCRIPTION OF THE DRAWINGS

FIG. 4 is a black-and-white drawing of twigs, mature leaves and fruit.

DESCRIPTION OF THE NEW PLANT

Figure 1:
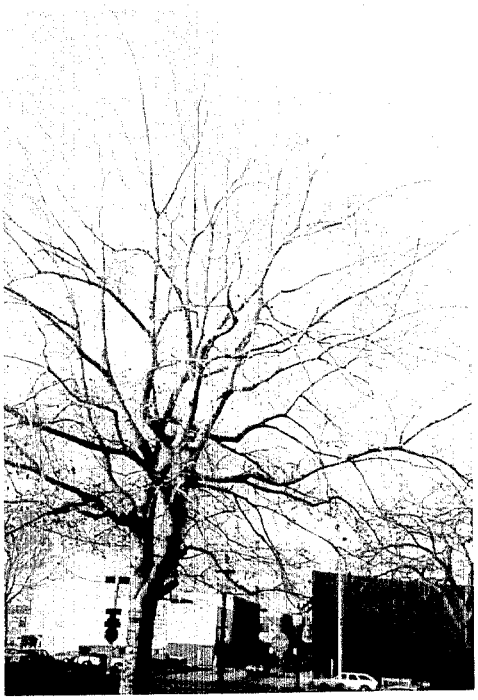
FIG. 1 is a photographic view disclosing my new variety as it appears with foliage.
Figure 2:
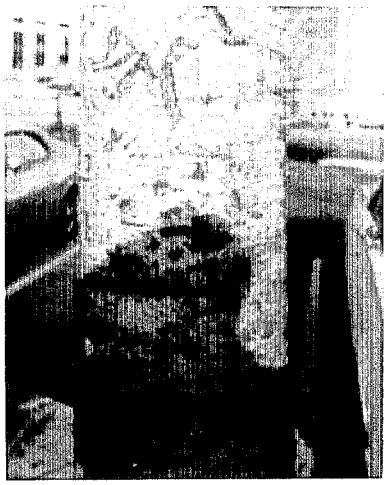
FIG. 2 is a photographic close-up view of the bark.
Figure 3:
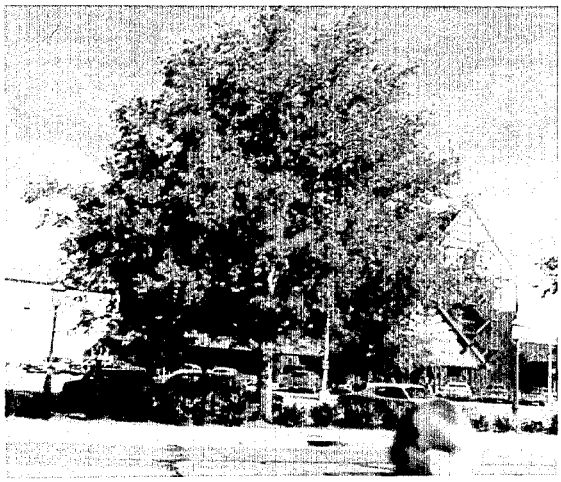
FIG. 3 is a photographic view showing the new variety taken in the summertime.

The following is a detailed description of my new variety sugar hackberry tree, the stated observations having been made of trees growing at Urbana, Ill. by applicant and found to distinguish from the species.

Origin: Seedling.
Parentage: Variety of *C. laevigata* Willd.
Classification: *Celtis laevigata.*
Form: Tree.
Shape: Principally smooth with occasional ridges.
Height: 60 to 80 feet.
Trunk size: 40.3 cm. D.B.H. as compared to 38 normal hackberry trees, which average 24.3 D.B.H.
Growth rate: Rapid for species with a heavier, fuller crown.
Bark: Light gray, smooth, with numerous wart-like excrescences arranged horizontally around the trunk.
Branches: Numerous.
- *Angle of attachment.*—From 35° to 45° from main stem with no V-crotches.
- *Size.*—Major branches — 9.9 - 10.8 cm.
- *Spacing.*—Variable, averaging 34".
- *Bark.*—Light gray, smooth.
- *Twigs.*—Measured 1.5 cm. from terminus are 1.06 mm., as compared to twigs of the species being 0.56 mm.

Leaves:
- *Length.*—4 to 6.5 cm.
- *Width.*—2 to 3.5 cm.
- *Form.*—Narrowly to broadly ovate with long, tapering, often curved tips, rounded and often assymetrical bases.
- *Margin type.*—Entire to slightly repand.
- *Texture.*—Medium.
- *Pubescence distribution.*—Glabrous above and below.
- *Quantity.*—Abundant.
- *Petioles.*—0.6-1.0 cm. long.
- *Ribs and veins.*—One primary rib with several lateral veins.
- *Thorns, spines and prickles.*—None.
- *Winter buds.*—Appressed to stems, 2 to 2.8 mm. long mostly 2-ranked, with 3-5 imbricate, 2-ranked bud scales.
- *Fruit.*—Solitary, globose, bright orange-red drupe 7 mm. in diameter with firm outer coat and a thin fleshy layer therebeneath with a hard stone approximately 5 mm. in diameter, with the pedicels 7 to 10 mm. long.

This new variety most resembles *Celtis laevigata* but clearly distinguishes from it by the dense branching habit, dense leaves and superior growth form having a heavier, fuller crown than the normal specie. It has, as a dormant tree, 60.9 percent denser branches in the crown as compared to the heaviest crown of the normal specie. This new variety has proved very hardy in temperatures of below −20°, with no breakage through many ice storms, and after twenty years growth, the parent has shown no Witches Broom twig disease. The instant variety does not have a multitude of small twigs as does *C. laevigata.* The above distinctions and observations were made by applicant by viewing many hundreds of *C. laevigata* trees in his nursery.

I claim:

1. A new and distinct variety of sugar hackberry tree, substantially as herein shown and described, characterized by its rapid growth having a profusion of lateral branches and leaves with a heavier and well balanced crown with a heavier branch density, its very hardy growth habit showing hardiness at below −20° F., freedom from Witches Broom twig disease, and having less and heavier twig diameter.

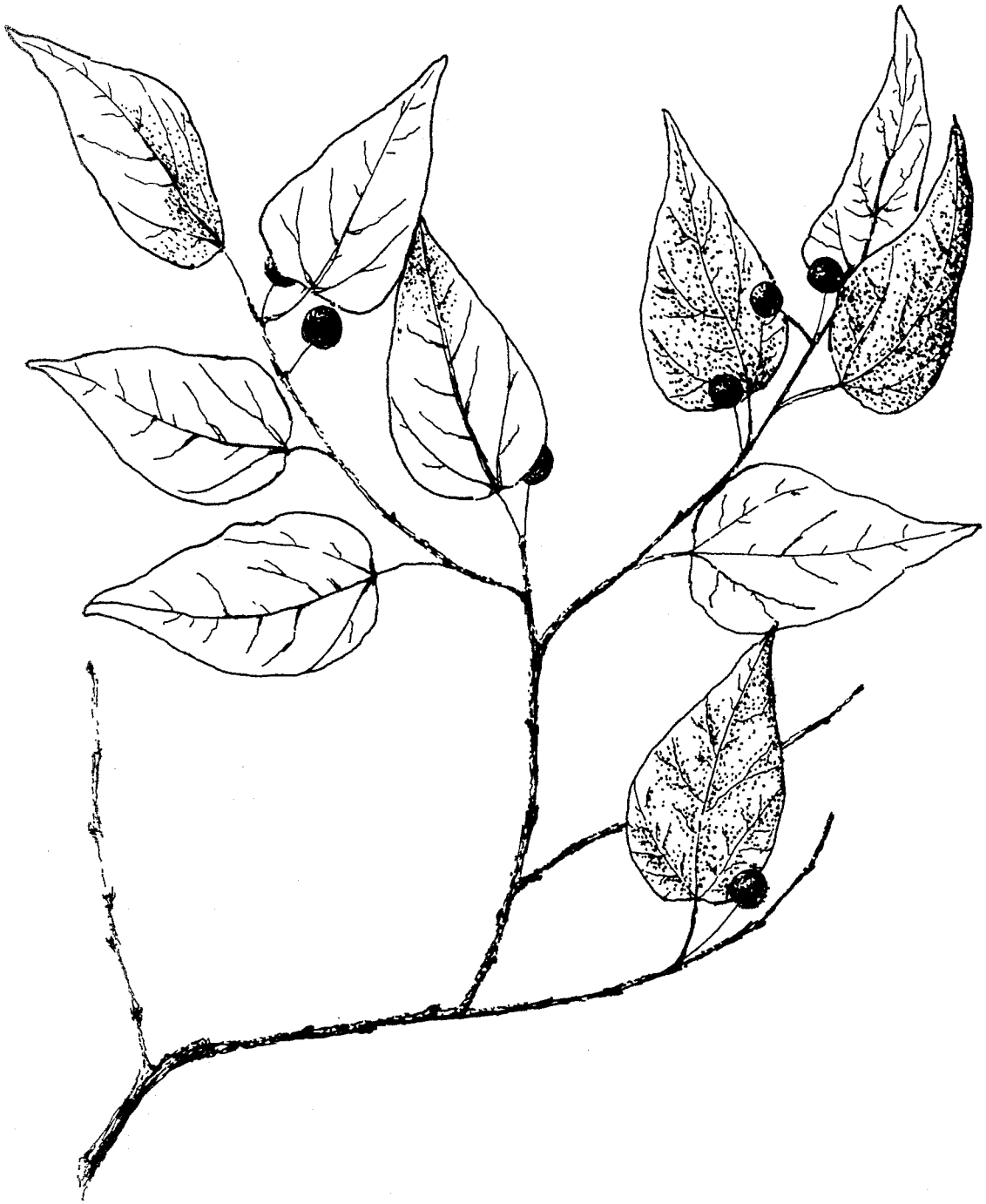

* * * * *